United States Patent [19]

Menon et al.

[11] Patent Number: 5,675,052

[45] Date of Patent: Oct. 7, 1997

[54] HYDROCARBON ALKYLATION PROCESS

[75] Inventors: Raghu Menon, Medford; Ramakrishnan Ramachandran, Allendale; Virginia Malik, Linden; Martin Bülow, Basking Ridge, all of N.J.

[73] Assignee: The BOC Group, Inc., New Providence, N.J.

[21] Appl. No.: 528,959

[22] Filed: Sep. 15, 1995

[51] Int. Cl.$^6$ .................................... C07C 2/56; C07C 7/12
[52] U.S. Cl. .......................... 585/717; 585/709; 585/818; 585/822; 208/308
[58] Field of Search .................................... 585/717, 709, 585/822, 818; 208/308

*Primary Examiner*—Glenn A. Caldarola
*Assistant Examiner*—In Suk Bullock
*Attorney, Agent, or Firm*—Coleman R. Reap; Salvatore P. Pace

[57] ABSTRACT

A hydrocarbon stream is cracked to produce a hot gaseous stream which is compressed and cooled to condense almost all of the hydrocarbons contained in the stream. A noncondensed stream remaining after the condensation step, comprised predominantly of hydrogen and $C_1$ to $C_3$ hydrocarbons, is subjected to pressure swing adsorption or temperature swing adsorption at an adsorption temperature of about 0° to about 250° C. in a bed of adsorbent which selectively adsorbs ethene and propene, thereby adsorbing substantially all of the ethene and propene from the gas stream. The ethene and/or propene is recovered upon bed regeneration. Higher alkenes are separated from alkanes by various methods.

31 Claims, 4 Drawing Sheets

5,675,052

HYDROCARBON ALKYLATION PROCESS

FIELD OF THE INVENTION

This invention relates to the alkylation of hydrocarbons and more particularly to the alkylation of butenes and propene with isobutane.

BACKGROUND OF THE INVENTION

The production of premium quality motor fuels by alkylation of alkanes with alkenes has been practiced since the late 1930s. The fuels are generally produced by the addition reaction of an i-alkane, particularly i-butane, with $C_2$ to $C_5$ alkenes. Alkylates produced from $C_3$ and $C_4$ monoolefins and isobutane are especially valued since these alkylates have good octane values and are clean burning, and the $C_3$ and $C_4$ reactants are readily available as products of hydrocarbon catalytic cracking processes. However, prior to use in alkylation processes, certain components of the $C_3$ and $C_4$ streams, particularly propane and normal-butane, are removed from the streams, since they are not suitable for alkylation.

The $C_3$ and $C_4$ feed streams used in alkylation plants are usually derived from hydrocarbon cracking plants. The overhead gas stream from the cracking unit contains an array of lower hydrocarbons, ranging from methane to $C_5$ and higher hydrocarbons. This stream is subjected to a series of distillation and absorption steps to remove most of the $C_5$ and heavier liquid hydrocarbons and the $C_2$ and lighter gaseous components. The remaining stream is comprised substantially of $C_3$ and $C_4$ hydrocarbons. To separate the components of this stream, the stream is generally sent to a depropanizer, which separates the stream into a $C_3$ overhead stream and a $C_4$ bottoms stream. If it is desired to use propene from the $C_3$ stream for the production of alkylates, the $C_3$ stream is sent to a $C_3$ splitter, where propane and propene are separated. The propane is sent to fuel or storage, and the propene is retained for use in the alkylation process. Separating propene from propane is very difficult and costly, because it requires a distillation column or pair of columns having about 150 or more theoretical stages to effect satisfactory separation of these compounds.

The $C_4$ bottoms stream from the depropanizer is comprised of normal butane (n-butane), methylpropane or isobutane (i-butane), butene-1, butene-2 (cis- and trans- species) and methylpropene or isobutylene (i-butylene). Since i-butane is the paraffin of interest for use in most alkylation processes, it is desirable to separate this component from the n-butane contained in the bottoms stream. This can be accomplished by subjecting the $C_4$ stream to distillation in a deisobutanizer, from which the i-butane, i-butylene and butene-1 are generally recovered together as the overhead product, and n-butane and the butene-2 species are recovered from the debutanizer bottoms stream. Since n-butane is not desired as a reactant in alkylation processes while the butene-2 species are, it is preferred to recover the butene-2 species from the bottoms product. However, as is the case with the propane-propene distillation, separation of these $C_4$ compounds by distillation is very difficult, since n-butane and the 2-butenes have boiling points very close to each other.

Processes that will reduce the overall cost of separating the various lower alkanes and alkenes and alkylating hydrocarbons are continuously sought. The present invention provides such a process.

SUMMARY OF THE INVENTION

In the process of the invention, a hydrocarbon feed stream comprised substantially of $C_3$ and $C_4$ saturated and ethylenically unsaturated hydrocarbons is subjected to a novel series of steps to separate the hydrocarbons that are desired for use in alkylation processes from those that are of no use in such processes, and the desired hydrocarbons are subjected to an alkylation process. As part of the alkylation process, n-butane in the gas stream may be isomerized to i-butane.

According to a first embodiment of the invention, the hydrocarbon feed stock is subjected to a pressure swing adsorption process using an adsorbent which more strongly adsorbs propene and n-butenes than the other components of the feed stock, thereby producing a nonadsorbed fraction comprised of the saturated hydrocarbons and the branched $C_4$ hydrocarbon components of the feed stock, and an adsorbed fraction, comprising propene and the n-butenes. The nonadsorbed fraction is then subjected to a second separation step which effects the separation of the nonadsorbed $C_4$ hydrocarbons from the other components of the nonadsorbed fraction. The second separation may be effected by distillation, by adsorption using an adsorbent which more strongly adsorbs $C_4$ hydrocarbons than the other components of this stream, or by membrane separation using a membrane which is impermeable to $C_4$ hydrocarbons but which is permeable to the other components of the nonadsorbed fraction. The propene- and n-butene-rich fraction is desorbed and the desorbed fraction and the $C_4$ hydrocarbons are subjected to an alkylation process, thereby producing high octane gasoline.

According to a second embodiment of the invention, the hydrocarbon feed stock is first subjected to a separation process which effects the separation of the $C_3$ and $C_4$ hydrocarbons. This separation, which is similar to the second separation of the first embodiment, may be effected by distillation, by adsorption using an adsorbent which more strongly adsorbs $C_4$ hydrocarbons than the other components of the feed stock, or by membrane separation using a membrane which is impermeable to $C_4$ hydrocarbons but which is permeable to the other components of the feedstock. The $C_3$ hydrocarbon stream is then subjected to a pressure swing adsorption process using an adsorbent which more strongly adsorbs propene than propane, thereby producing a propene-enriched adsorbed fraction and a propane-enriched nonadsorbed fraction. A propene-enriched fraction is desorbed from the adsorbent, and the desorbed fraction and the $C_4$ hydrocarbons are subjected to an alkylation process, thereby producing high octane gasoline.

In a specific embodiment of the invention, the feed stream is introduced into an alkylation plant system downstream of the acid settler, preferably by combining this stream with the overhead stream from the acid settler to the $C_3$–$C_4$ splitter. The $C_3$–$C_4$ splitter overhead stream, comprised substantially of propene and propane, is sent to an adsorption system containing an adsorbent which preferentially adsorbs propene. The nonadsorbed gas product stream from the adsorption system, comprised of propane-enriched gas, is sent to LPG storage, and the adsorbed stream, comprised of propene-enriched fraction is desorbed and added to the feed to the alkylation plant. The bottoms stream from the $C_3$–$C_4$ splitter, comprised substantially of $C_4$ hydrocarbons, is sent to a deisobutanizer column, wherein it is split into an overhead stream containing i-butane, i-butylene and 1-butene, an intermediate-boiling side stream containing n-butane and the 2-butenes and a bottoms product comprising alkylate. The overhead stream from the deisobutanizer can be sent directly to the alkylation unit, and the side stream consisting of n-butane and the 2-butenes is sent to an adsorption system containing an adsorbent which preferentially adsorbs 2-butenes. The 2-butenes, upon desorption, can be used as alkylation reactor feedstock. The nonadsorbed product stream from this unit, comprised of n-butane-enriched fraction is sent to product storage or to an isomerization plant to be converted to i-butane for use in the alkylation plant.

In a preferred aspect of each embodiment of the invention, n-butane is subjected to an isomerization process to convert the n-butane to i-butane prior to the alkylation process.

The propene and n-butenes adsorption step of the first embodiment and the propene-propane adsorptive separation step of the second embodiment may be carried out as a pressure swing adsorption (PSA) process or a temperature swing adsorption (TSA) process. These processes are typically carried out at a temperature in the range of about 0° C. to about 250° C., and are preferably carried out at a temperature above about 50° C. They are generally carried out at an absolute pressure in the range of about 0.2 to 20 bar, and are preferably carried out at an absolute pressure of about 1 to 5 bar.

In a preferred embodiment of the invention, the adsorbent used in the n-butenes and propene adsorption step of the first embodiment and the propene-propane separation step of the second embodiment is a type A zeolite, and in the most preferred embodiment, it is 4A zeolite. When these separations are by PSA, the pressure during the regeneration step is reduced, usually to an absolute pressure in the range of about 100 to about 5000 millibar, and preferably to an absolute pressure in the range of about 100 to about 2000 millibar. When they are carried out by TSA, the bed temperature is usually raised during bed regeneration to a value in the range of about 100° to about 350° C., and is preferably raised to a value in the range of about 150° to 300° C.

The $C_4$ separation step, i.e. the step in which the $C_4$ hydrocarbons are separated from the $C_3$ and lighter hydrocarbons, which, in the description of the first embodiment, is referred to as the second separation step, is preferably carried out by distillation or by adsorption. In the most preferred embodiment this separation is carried out by distillation.

When the $C_4$ separation is carried out by adsorption, it is preferable to use a PSA process, the adsorption step of which is most preferably carried out at an absolute pressure in the range of about 2 to about 5 bar, and the adsorbent regeneration step of which is most preferably carried out at an absolute pressure in the range of about 200 to about 2000 millibar.

When the $C_4$ separation is carried out by adsorption, the preferred adsorbent is 5A zeolite or dealuminated Y zeolite (DAY) or mixtures of these.

DETAILED DESCRIPTION OF THE INVENTION

The process of the invention separates hydrocarbon feed materials that are most desirable for alkylation from the other light hydrocarbons in the feedstock. The most desirable alkane for alkylation is i-butane, and the most desirable alkenes are the butenes, particularly the 2-butenes. The other butenes and propene are also useful in alkylation, but produce a somewhat lower octane gasoline product.

The feedstock used in the invention comprises $C_3$ hydrocarbons, i.e. propane and propene, and $C_4$ hydrocarbons, i.e. n-butane and/or i-butane and one or more butenes, i.e. butene-1, cis-butene-2 and/or trans-butene-2. The feed may also contain $C_2$ hydrocarbons, i.e. ethane and/or ethene, which behave like propane and propene, respectively, in the various separations described herein. Although the feedstock can be obtained from other sources, it is conveniently obtained as hydrocarbon cracking product, such as the overhead stream from a wet gas debutanizer unit, which is usually located downstream of a hydrocarbon catalytic or thermal cracking unit. In a preferred aspect of the invention, the feedstock is comprised primarily of $C_3$ and $C_4$ hydrocarbons, which simplifies the separation and results in the production of higher octane alkylated products.

The invention can be better understood from the accompanying drawings. Auxiliary equipment not necessary for an understanding of the invention, including compressors, heat exchangers and valves, has been omitted from the drawings to simplify discussion of the invention.

Figure 1:
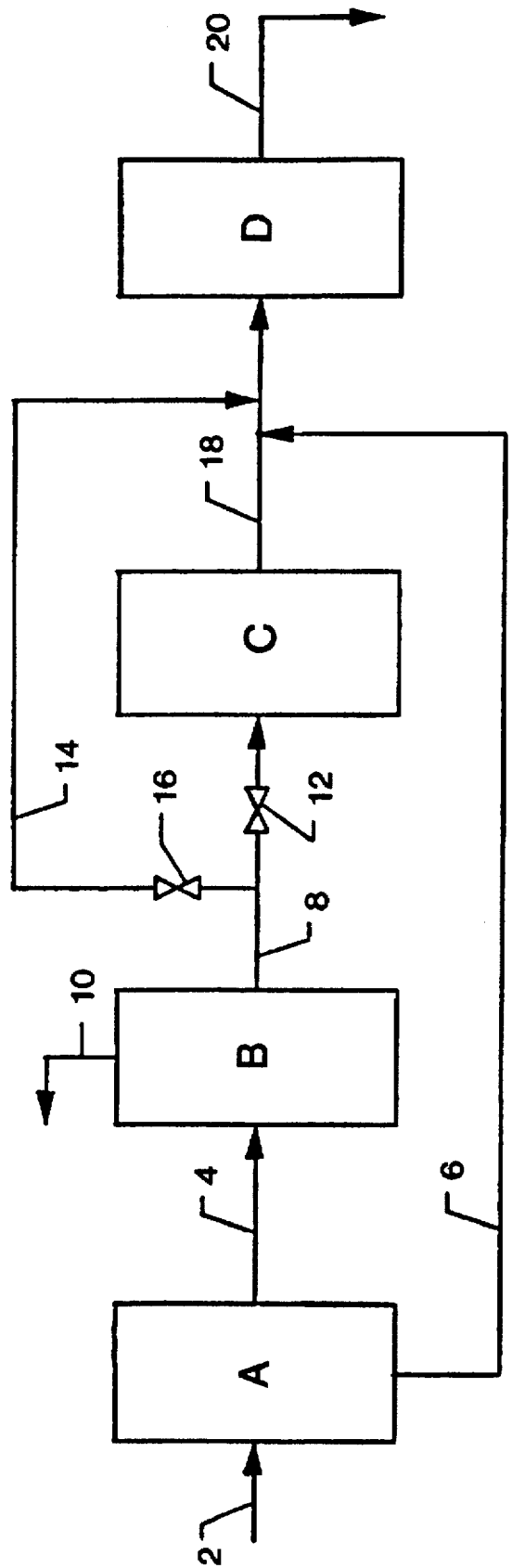
FIG. 1 illustrates, in a block diagram, a first embodiment of the present invention.
Figure 2:
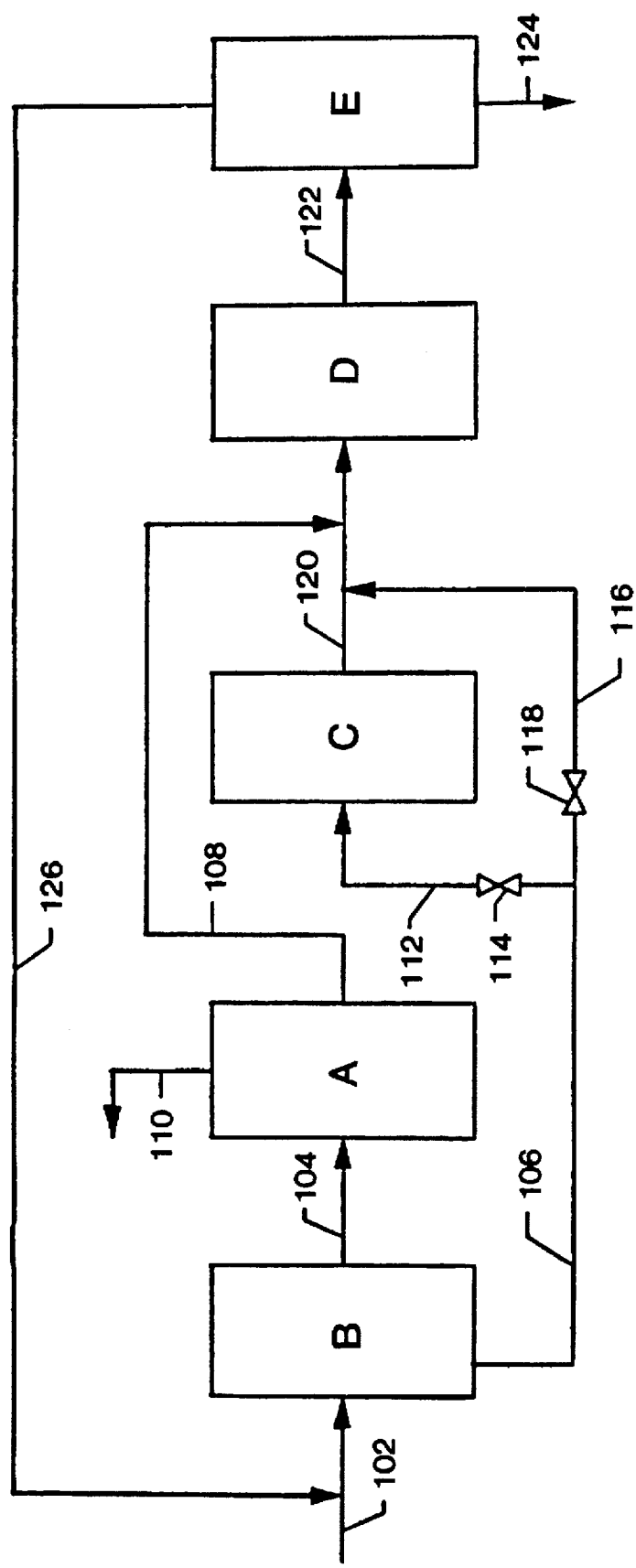
FIG. 2 illustrates, in a block diagram, a second embodiment of the invention.

In FIGS. 1 and 2, A is an adsorption-based propene-propane separator, B is a $C_4$ separation plant, optional unit C is a $C_4$ isomerization plant, and D is an alkylation plant.

The function of separator A is to separate the linear alkenes, i.e. propene and normal butenes (and ethene, if present) from the other components of the feedstock. It is typically a pressure swing adsorption or temperature swing adsorption system, generally comprising two or more stationary beds arranged in parallel and adapted to be operated in a cyclic process comprising adsorption and desorption. In such systems the beds are cycled out of phase to assure a pseudo-continuous flow of alkene-enriched gas from the adsorption system.

The beds of separator A are packed with an adsorbent which selectively adsorbs alkenes from a gas mixture containing the alkenes and one or more alkanes. In general, the adsorbent may be alumina, silica gel, microporous silica, zeolites, carbon molecular sieves, etc. Typical adsorbents include alumina, silica gel, carbon molecular sieves, zeolites, such as type A and type X zeolite, type Y zeolite, etc. The preferred adsorbents are type A zeolites, and the most preferred adsorbent is 4A zeolite.

Zeolite 4A, i.e. the sodium form of type A zeolite, has an apparent pore size of about 3.6 to 4 Å (angstrom units), depending on temperature. This adsorbent provides enhanced selectivity and capacity in adsorbing ethene from ethene-ethane mixtures and propene from propene-propane mixtures at elevated temperatures. This adsorbent is most effective for use in the invention when it is substantially unmodified, i.e. when it has only sodium ions as its exchangeable cations. However, certain properties of the adsorbent, such as transport behavior of the adsorbed species and catalytic, thermal and hydrothermal stability, may be improved by partly exchanging some of the sodium ions with other cations. Accordingly, it is within the scope of the preferred embodiment of the invention to use a type zeolite 4A in which some of the sodium ions contained in the adsorbent are replaced with other metal ions, provided that the percentage of ions exchanged is not so great that the adsorbent loses its 4A character. Among the properties that characterize 4A zeolite are its ability to selectively adsorb ethene from ethene-ethane mixtures and propene from propene-propane gas mixtures at elevated temperatures, and to accomplish this result without causing significant oligomerization or polymerization of the alkenes present in the mixtures. In general, it has been determined that up to about 25 percent (on an equivalent basis) of the sodium ions in 4A zeolite can be replaced by ion exchange with other cations without divesting the adsorbent of its 4A character. Cations that may be ion exchanged with the 4A zeolite used in the alkene-alkane separation include, among others, calcium, magnesium, strontium, zinc, cobalt, silver, copper, manganese, cadmium, etc. When exchanging other cations for sodium ions it is preferred that less than about 10 percent of the sodium ions (on an equivalent basis) be replaced with such other cations.

Another class of preferred adsorbents are those which contain certain oxidizable metal cations, such as copper-containing adsorbents, which possess enhanced adsorptive capacity and selectivity with respect to the preferential adsorption of alkenes from gaseous alkene-alkane mixtures. Suitable adsorbent substrates for manufacturing copper-modified adsorbents carrying, in particular, cuprous ions, include silica gel, and zeolite molecular sieves, such as zeolite 4A, zeolite 5A, zeolite type X, zeolite type Y and MFI-type zeolites, such as silicalite. The manufacture and use of copper-modified adsorbents and examples of suitable copper-containing adsorbents are set forth in U.S. Pat. No. 4,917,711, the disclosure of which is incorporated herein by reference.

Separator A is provided with feed line 2, nonadsorbed gas discharge line 4, and desorbed gas discharge line 6. Line 4 connects the nonadsorbed gas outlet of separator A to the inlet of $C_4$ separator B.

The purpose of separator B in the system of FIG. 1 is to effect the separation of the $C_4$ hydrocarbons from the remainder of the gas stream. Separator B can be a distillation unit, an adsorption system, or a semipermeable membrane separator. Separator B is preferably a distillation column or an adsorption system. Distillation columns are the most preferred because of the ease of separating the components of this stream by this technique. Since the components of the separator B feed stream other than the $C_4$ hydrocarbons are propane and perhaps ethane, the $C_4$ components can be easily separated from these components by distillation. In a distillation operation, the $C_4$ components are recovered as a bottoms product stream, and the lighter gases are removed as an overhead stream.

Separator B can also be an adsorption system. In this case the adsorbers of the system are packed with one or more adsorbents that adsorb the $C_4$ hydrocarbons remaining in the process stream, particularly i-butane, more strongly than propane and ethane. Suitable adsorbents include molecular sieves, activated carbons, activated clays, silica gels, microporous silica obtained from sol-gel processes, activated aluminas, etc. Molecular sieves include aluminophosphates, silicoaluminophosphates, and zeolites. Typical zeolites include natural zeolites, such as chabazite, clinoptilolite, erionite, mordenite, etc., and synthetic zeolites, such as type A zeolites, type X and Y zeolites, and MFI-type zeolites, such as silicalite. Preferred adsorbents include silica gel, activated carbon, activated alumina, zeolite molecular sieves and mixtures of these. Although these adsorbents also adsorb propane and lower alkanes, they adsorb $C_4$ hydrocarbons more strongly; hence the $C_4$ hydrocarbons will displace lower hydrocarbons that are retained in the adsorbent. Adsorption is preferred over membrane separation because of the lower capital investment and energy requirements of this procedure.

Separator B can also be a membrane separator. Since the $C_4$ hydrocarbons are considerably larger in molecular size than propane and the lower hydrocarbons, membranes are available that will retain the $C_4$ hydrocarbons and permit the other components of the stream to pass through.

Separator B is provided with $C_4$ hydrocarbon discharge line 8 and propane and lighter gas discharge line 10.

Optional isomerization plant C can be any unit or system that effects the isomerization of n-butane to i-butane. This plant generally comprises a reactor that is charged with a catalyst, such as aluminum chloride. The plant is normally operated at a temperature in the range of about 90° to about 125° C. and pressures in the range of about 10 to about 25 bar, absolute. The lower hydrocarbons do not undergo isomerization; hence there is no need to separate these components from the n-butane prior to isomerization. 1-Butene present in the isomerization plant feed may undergo isomerization to i-butylene, but this will not adversely affect the octane value of the alkylated product, and may actually improve it, since alkylates produced from i-butane and i-butene have slightly higher octane values than those produced from i-butane and 1-butene.

In FIG. 1, line 8 connects the $C_4$ discharge end of separator B with the feed inlet of isomerization plant C. Valve 12 controls flow through line 8. Line 8 is also connected to bypass line 14, which bypasses isomerization plant C. Line 14 is fitted with valve 16, which controls flow therethrough. On its outlet end isomerization plant C is provided with isomerized product discharge line 18, which is joined to the inlet of alkylation plant D. In the embodiment illustrated in FIG. 1, lines 6 and 14 join line 16 upstream of the feed inlet of alkylation plant D. On its outlet end, alkylation plant D is provided with alkylate discharge line 20.

In practicing the process of the invention in the system illustrated in FIG. 1, a hydrocarbon feed stream containing $C_3$ and $C_4$ hydrocarbons, and perhaps methane and $C_2$ hydrocarbons, is introduced into separator A and subjected to adsorption. The temperature at which the adsorption step is carried out depends upon a number of factors, such as the particular adsorbent being used, e.g. unmodified 4A zeolite, a particular metal-exchanged 4A zeolite or another adsorbent which selectively adsorbs alkenes from alkene-alkane mixtures, and the pressure at which the adsorption is carried out. In general, the adsorption step is carried out at a minimum temperature of about 0° C., is preferably carried out at a minimum temperature of about 50° C., and is most preferably carried out at a temperature of at least about 70° C. The upper temperature limit at which the adsorption step in unit A is carried out is determined mostly by economics. In general, the adsorption step is desirably carried out at a temperature below the temperature at which the alkene undergoes chemical reaction, such as oligomerization and polymerization. The practical upper adsorption temperature limit is about 250° C. When unmodified 4A zeolite is used as the adsorbent, the process is generally carried out at or below 200° C., and is preferably carried out at a temperature at or below 170° C. Oxidizable metal-containing adsorbents, such as copper-modified adsorbents, are particularly effective at temperatures above about 100° C., such as, for example, temperatures between about 100° C. and 250° C. Adsorption processes using these adsorbents are preferably carried out at temperatures in the range of about 110° to 200° C., and most preferably at temperatures in the range of about 125° to about 175° C.

The pressures at which the adsorption step is carried out generally ranges from about 0.2 to about 20 bar, and preferably from about 1 to 10 bar for pressure swing adsorption cycles, and is usually about atmospheric or above for temperature swing adsorption cycles.

When the adsorption process is straight PSA the regeneration step is generally carried out a temperature in the neighborhood of the temperature at which the adsorption step is carried out and at an absolute pressure lower than the adsorption pressure. The pressure during the regeneration step of PSA cycles is usually in the range of about 20 to about 5000 millibar, and preferably in the range of about 100 to about 2000 millibar. When the adsorption process is TSA, bed regeneration is carried out at a temperature higher than the adsorption temperature, usually in the range of about 100° to about 350° C., and preferably in the range of about 150° to 300° C. In the straight TSA embodiment, the pressure is generally the same during the adsorption and regeneration steps, and it is often preferred to conduct both steps at about atmospheric pressure or above. When a combination of PSA and TSA is used the temperature and pressure during the bed regeneration step are higher and lower, respectively, than they are during the adsorption step.

During the adsorption step of the process, the linear alkenes, i.e. ethene, propene, and the n-butenes, are adsorbed from the feed gas by the adsorbent, and the alkanes and branched-chain alkenes, i.e. propane, n-butane, i-butane, and i-butylene pass through the adsorbent and leave separator A through line 4.

When the alkenes adsorption front traveling through the vessel(s) of separator A in which the adsorption step is being carried out reaches the desired point in the vessel(s), the adsorption process in these vessel(s) is terminated and these vessels enter the regeneration mode. During regeneration, the alkene-loaded vessels are depressurized, if the adsorption cycle is pressure swing adsorption, or heated, if a temperature swing adsorption cycle is employed. As the regeneration proceeds, alkene-enriched gas is discharged from separator A through line 6.

The method of regeneration of the adsorption beds depends upon the type of adsorption process employed. In the case of pressure swing adsorption, the regeneration phase generally includes a countercurrent depressurization step during which the beds are vented countercurrently until they attain the desired lower pressure. If desired, the pressure in the beds may be reduced to subatmospheric pressure by means of a vacuum inducing device, such as a vacuum pump (not shown).

In some cases, in addition to the countercurrent depressurization step(s), it may be desirable to countercurrently purge the bed with the nonadsorbed product gas stream exiting separator A. In this case the bed(s) may be countercurrently purged with nonadsorbed gas, and the purge step is usually initiated towards the end of the countercurrent depressurization step, or subsequent thereto. During the purge step, the purge gas can be introduced into separator A via line 4 from an intermediate storage facility in line 4 (not shown), when separator A comprises a single adsorber; or from another adsorber that is in the adsorption phase, when separator A comprises multiple adsorbers arranged in parallel and operated out of phase. In a preferred method of operation, all or a portion of the purge gas and purged stream is recycled to the feed end of separator A for reprocessing.

The adsorption cycle may contain steps other than the fundamental steps of adsorption and regeneration. For example, it may be advantageous to depressurize the adsorption bed in multiple steps, with the first depressurization product being used to partially pressurize another bed in the adsorption system. This will further reduce the amount of gaseous impurities transferred to line 4. It may also be desirable to include a cocurrent purge step between the adsorption phase and the regeneration phase. The cocurrent purge is effected by terminating the flow of feed gas into separator A and passing highly purified alkene cocurrently into the adsorption bed at adsorption pressure. This has the effect of forcing nonadsorbed gas contained in the void spaces in separator A toward the nonadsorbed gas outlet, thereby ensuring that the alkene produced during the countercurrent depressurization will be of high purity. The alkene used for the cocurrent purge can be obtained from an intermediate storage facility in line 6 (not shown), when separator A comprises a single adsorber; or from another adsorber that is in the adsorption phase, when separator A comprises multiple adsorbers arranged in parallel and operated out of phase.

The nonadsorbed gas stream exiting adsorption plant A through line 4 next enters separator B, wherein the $C_4$ components are separated from the $C_3$ and lighter components of this stream. This separation is preferably accomplished by distillation. The conditions of suitable distillation procedures are well known and require no detailed explanation. The $C_3$ and lighter components boil at considerably lower temperatures than the $C_4$ components and thus can be easily separated from the more desirable $C_4$ components. The $C_3$ and lighter components are removed from separator B through line 10, and the $C_4$ components are discharged from this unit through line 8.

If the $C_4$ stream from separator B contains significant quantities of n-butane, it may be preferred to subject this stream to isomerization to convert the n-butane to i-butane. In this case valve 12 in line 8 is opened and valve 16 in line 14 is closed, and the separator B effluent enters isomerization plant C through line 8, and undergoes isomerization by well known processes using any of various isomerization catalysts, such as aluminum chloride. The isomerized $C_4$ stream, now enriched in i-butane leaves unit C via line 18.

If the $C_4$ stream from separator B is comprised substantially of i-butane, it is preferred to have this stream bypass isomerization unit C and go directly to alkylation plant D. In this case, valve 16 is opened and valve 12 is closed, and the $C_4$ stream from separator B passes to alkylation plant D through line 14. In the embodiment illustrated in FIG. 1, the streams in lines 6 and 14 join and together enter alkylation plant D. Depending upon the particular alkylation process used in the process of the invention, these streams may enter the alkylation plant together or they may enter it separately.

The alkylation step is not critical and any of the various known processes may be used. The most common processes use sulfuric acid or hydrofluoric acid as the catalyst. The conditions under which the alkylation process is carried out forms no part of the present invention. The product stream leaving alkylation plant D through line 20 contains the high octane alkylate product, various unconsumed reactants, and certain byproducts, such as propane. This mixture is usually sent to a separator, or series of separators for separation of the high octane alkylate product from the alkylation reactants and nonreactive components stream. The alkylate is usually sent to storage or gasoline blending, and the mixed reactant and nonreactive component stream is recycled to a separator, for example separator A or separator B, for reprocessing.

The system illustrated in FIG. 2 is similar to that of FIG. 1, except that the positions of units A and B are reversed, and the system includes as additional unit, separator E. In the process of the FIG. 2 embodiment, the hydrocarbon feed stream enters separator B through line 102 and is separated therein into a $C_4$ stream, which leaves this unit through line 106, and a $C_3$ and lighter stream, which leaves separator B through line 104. The $C_3$ and lighter stream next enters separator A and is separated therein into a propene stream, which exits this unit through line 108, and a propane-enriched stream, which exits unit A through line 110 and is sent to LPG or is otherwise disposed of.

The $C_4$ stream exiting separator B can be subjected to isomerization in unit C, if this stream contains significant quantities of n-butane; or it can be sent directly to alkylation plant D, if it is comprised substantially of i-butane. If this stream is to be subjected to isomerization, valve 114 in line 112 is open and valve 118 in line 116 is closed, and if it is to be directly alkylated, valve 114 is close and valve 118 is open.

The streams in lines 108 and 116 enter alkylation plant D together or separately, as discussed above, and the alkylated product stream leaves plant D through line 122. Subsequent to acid recovery, this stream next enters separator E, which can be any separation means, such as a debutanizer or an adsorption system. The product stream entering separator E is separated into a high octane alkylate product, which leaves separator E through line 124, and a mixed stream containing unconsumed alkene and alkane reactants, and byproducts, including propane. The mixed stream leaves separator E through line 126, and, in the embodiment illustrated in FIG. 2, it is recycled to separator B via line 102 for reprocessing through the system.

Figure 3:
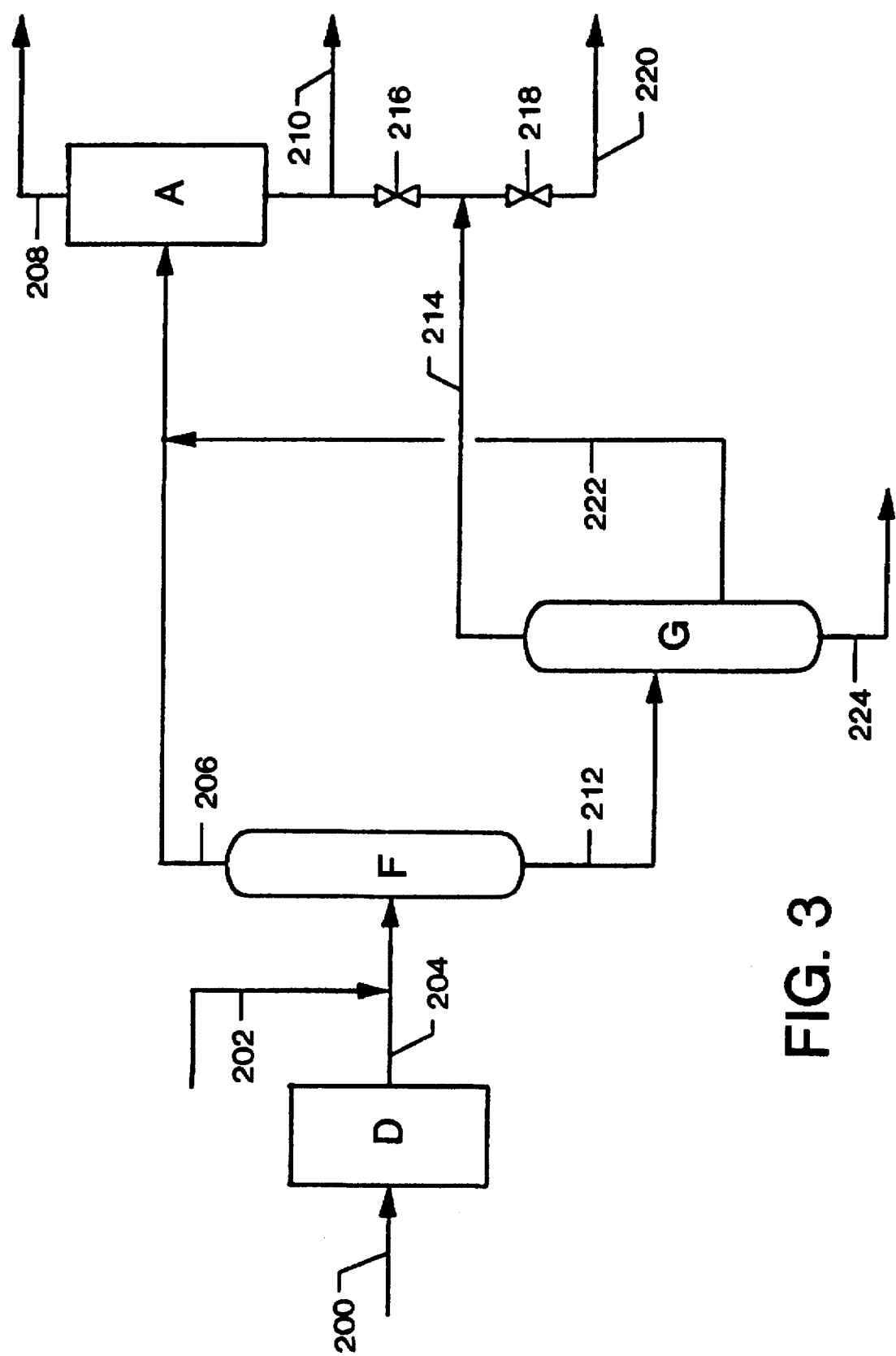
FIG. 3 illustrates, in a block diagram, a specific embodiment of the invention.

The embodiment illustrated in FIG. 3 is a variation of the embodiments illustrated in FIGS. 1 and 2. The FIG. 3 system comprises, in addition to separator A, a $C_3$–$C_4$ splitter, F, and a deisobutanizer, G. The embodiment of FIG. 3 is illustrated as beginning with alkylation plant D, although it may be preceded by other units. The i-butane and alkene alkylation reactants enter plant D through line 200. Although FIG. 3 shows a single feed stream to alkylation plant D, it is to be understood that the various reactants and catalyst may enter this unit separately, the particular feed scheme depending on the particular alkylation process being employed. The product stream exiting alkylation plant D through line 204 contains the alkylate product, unreacted alkene and i-butane, feed and product propane, and perhaps other byproducts. Fresh feed from, for example, a refinery deethanizer, containing mixed $C_3$ hydrocarbons and mixed $C_4$ hydrocarbons enters line 204 through line 202. The combined stream enters separator F, which, for purposes of discussion is considered to be a $C_3$–$C_4$ distillation splitter, although it can be any separator which will separate $C_3$ and $C_4$ hydrocarbons. An overhead stream, comprised of propane and propene, leaves separator F through line 206 and next enters separator A, which, as discussed above is an adsorption system containing an adsorbent which more strongly adsorbs alkenes than alkanes. The propene entering this unit is adsorbed by the adsorbent, and the propane leaves separator A through line 208, and is sent to fuel or used for other purposes. Upon desorption, the propene leaves separator A through line 210.

The heavy product stream, comprised of $C_4$ hydrocarbons and alkylate product, leaves separator F through line 212 and enters separator G. Separator G can be any separator or series of separators capable of separating the components of the feed stream to this unit. For purposes of discussion separator G is considered to be a debutanizer distillation unit. The lighter boiling i-butane, together with i-butene and 1-butene, if present, leaves separator G through line 214.

This stream can then be combined with the stream in line 210 by opening valve 216 and closing valve 218, and the combined stream can be recycled to alkylation plant D via a recycle line (not shown). Alternatively, valve 216 can be closed and valve 218 opened, and this stream can be passed through line 220 and subjected to further treatment, or it can be recycled to alkylation plant D separately from the stream in line 210.

A middle cut from separator G, comprised mostly of 2-butenes and n-butane, leaves separator G through line 222. In the embodiment illustrated in FIG. 3, this stream joins the stream in line 206, and the mixed stream enters separator A. The 2-butenes are adsorbed with the propene by the adsorbent in separator A, and the n-butane passes out of separator A through line 208 with the nonadsorbed propane and is sent to refinery fuel, or subjected to further treatment. The 2-butenes leave separator A through line 210 and are returned to alkylation plant D with the propene.

The high octane alkylate product leaves separator G through line 224 and is sent to storage or gasoline blending.

Figure 4:
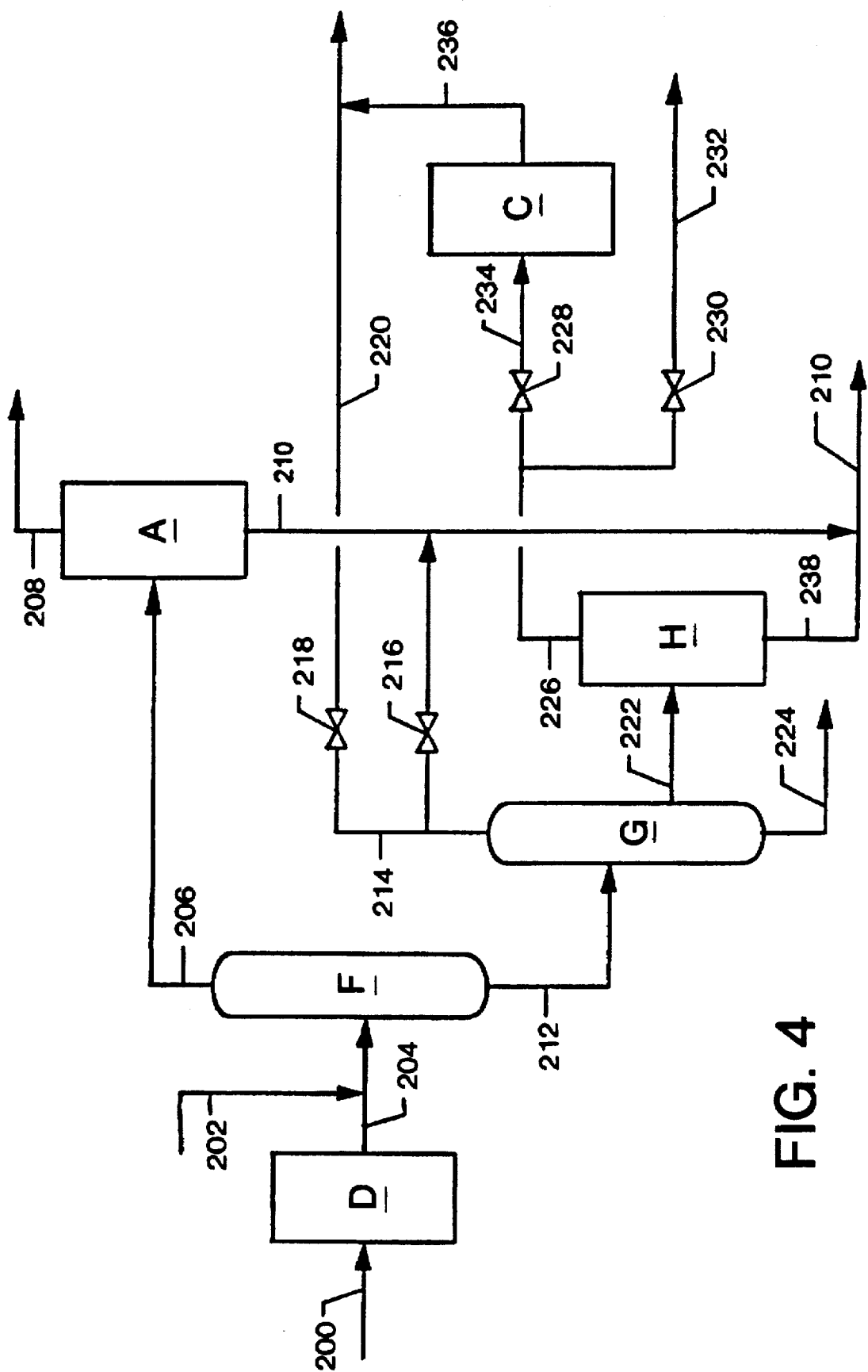
FIG. 4 illustrates, in a block diagram, a variation of the embodiment illustrated in FIG. 3.

The embodiment illustrated in FIG. 4 is a variation of the embodiment of FIG. 3. The FIG. 4 variation is valuable when the stream in line 202 contains a significant percentage of n-butane. In the system of FIG. 4, the middle cut stream leaving separator G through line 222 is not combined with the $C_3$ stream in line 206, as in the FIG. 3 embodiment, but instead, is treated separately. This stream enters separator H, which is an adsorption vessel containing an adsorbent which is selective for the separation of 2-butenes from n-butane. In general, the adsorbents useful in separator H can be any of those described above as useful in separator A. The particular adsorbent selected for use in separator H can be the same as or different from the adsorbent used separator A. The 2-butenes are adsorbed in separator H and the nonadsorbed stream, comprised mostly of n-butane, passes out of this unit through line 226. This stream can be sent to product storage by closing valve 228 and opening valve 230, in which case this stream leaves the system through line 232. However, in a preferred aspect of this embodiment, valve 228 is open and valve 230 is closed, and the n-butane-rich stream passes through line 234 and enters isomerization unit C. The n-butane is isomerized to i-butane in unit C, as described above, and the unit C product passes through line 236 and is combined with the i-butane in line 220. The combined stream is recycled to alkylation plant D through a recycle line (not shown).

The 2-butenes adsorbed in separator H are desorbed through line 238 and combined with the propene stream in line 210, and the combined stream is recycled to alkylation plant D.

It will be appreciated that it is within the scope of the present invention to utilize conventional equipment to monitor and automatically regulate the flow of gases within the system so that it can be fully automated to run continuously in an efficient manner.

An important advantage of the invention is that it permits separation of valuable alkenes from the relatively low value alkanes of light hydrocarbon cuts from a hydrocarbon cracking unit. It will be appreciated that a system that achieves enhanced selectivity, and hence increased overall recovery of alkenes from a cracking operation is highly beneficial from the perspectives of improved alkylation reactor utilization and the production of higher quality alkylate product.

Parts, percentages and ratios expressed in this specification are on a volume basis.

Although the invention has been described with particular reference to a specific experiment, this experiment is merely exemplary of the invention and variations are contemplated. For example, the process of the invention may be practiced in equipment arrangements other than those illustrated in the drawings. The scope of the invention is limited only by the breadth of the appended claims.

We claim:

1. A method of producing an alkylate of i-butane and propene, comprising the steps:
   (a) subjecting a mixture comprised of propene and propane to an adsorption process using a propene-selective adsorbent, thereby producing a propene-enriched fraction and a propane-enriched fraction;
   (b) subjecting a mixture comprised of i-butane and propane to a separation process selected from distillation, adsorption using an i-butane-selective adsorbent, membrane separation using a membrane which is impermeable to i-butane but permeable to propane, or combinations of these processes, thereby producing an i-butane-enriched fraction and a propane-enriched fraction; and
   (c) contacting said propene-enriched fraction with said i-butane-enriched fraction under conditions which effect the alkylation of i-butane with propene.

2. The method of claim 1, wherein said mixture comprised of i-butane and propane is the propane-enriched fraction produced in step (a).

3. The method of claim 1, wherein said mixture comprised of propene and propane is the propane-enriched fraction produced in step (b).

4. The method of claim 2 or claim 3, wherein said i-butane-enriched fraction contains n-butane, and said n-butane is isomerized to i-butane prior to step (c).

5. The method of claim 1, wherein the adsorption process of step (a) is selected from pressure swing adsorption, temperature swing adsorption or a combination of these.

6. The method of claim 5, wherein the adsorption phase of said adsorption process is conducted at a temperature above about 50° C.

7. The method of claim 5, wherein the adsorption phase of said adsorption process is conducted at a temperature in the range of about 50° to about 250° C.

8. The method of claim 1 or claim 7, wherein said propene-selective adsorbent is alumina, zeolite 4A, zeolite 5A, zeolite 13X, type Y zeolite or combinations of these.

9. The method of claim 8, wherein said propene-selective adsorbent contains an oxidizable metal ion.

10. The method of claim 9, wherein said oxidizable metal ion is cuprous ion.

11. The method of claim 10, wherein the adsorption step is carried out at a temperature between about 100° and about 250° C.

12. The method of claim 8, wherein said adsorbent is zeolite 4A.

13. The method of claim 12, wherein said adsorbent contains exchangeable cations other than sodium ions, but at a level insufficient to divest the adsorbent of its zeolite 4A character.

14. The method of claim 12, wherein the adsorption step is carried out at a temperature in the range of about 50° to about 200° C. and an absolute pressure in the range of about 0.2 to 100 bar.

15. The method of claim 12, wherein the adsorption step is carried out at a temperature in the range of about 70° to about 170° C. and an absolute pressure of about 1 to 50 bar.

16. The method of claim 8, wherein said adsorption process is pressure swing adsorption and said propene-selective adsorbent is regenerated at an absolute pressure in the range of about 0.02 to about 5 bar.

17. The method of claim 8, wherein said cyclic adsorption process is temperature swing adsorption and the bed is regenerated at a temperature in the range of about 100° to about 350° C.

18. The method of claim 1, wherein at least one of said mixture comprised of propene and propane and said mixture comprised of i-butane and propane is a cracked hydrocarbon stream.

19. The method of claim 18, wherein said cracked hydrocarbon stream is produced by catalytically cracking or thermally cracking a hydrocarbon stream.

20. The method of claim 1, wherein said propene-enriched fraction additionally contains at least one of ethene or a n-butene.

21. The process of claim 12, wherein said zeolite 4A contains copper ion and the adsorption phase of said adsorption process is carried out at a temperature in the range of about 125° to about 200° C.

22. The method of claim 2, wherein unreacted propene and i-butane from step (c) is recycled to the mixture being treated in step (a).

23. The method of claim 3, wherein unreacted propene and i-butane from step (c) is recycled to the mixture being treated in step (b).

24. The method of claim 23, wherein the effluent from step (c), containing alkylate, unreacted i-butane and unreacted propene, is recycled to the mixture being treated in step (b).

25. The method of claim 24, wherein the alkylate forms a part of the i-butane-enriched fraction and it is separated therefrom by distillation.

26. The method of claim 3 or claim 25, wherein said i-butane-enriched fraction additionally contains n-butane, and the n-butane is separated therefrom by distillation.

27. The method of claim 26, wherein the separated n-butane is isomerized to i-butane and subjected to the alkylation step of step (c).

28. The method of claim 1, wherein the separation process of step (b) is an adsorption process selected from PSA, TSA and a combination of these, and said i-butane selective adsorbent is dealuminated type Y zeolite.

29. The method of claim 28, wherein said adsorption process is PSA and said adsorbent is selected from dealuminated type Y zeolite, silicalite, microporous silica and mixtures of these.

30. The method of claim 29, wherein the adsorption step is carried out at an absolute pressure in the range of about 2 to about 5 bar and a temperature in the range of about 0° to about 75° C.

31. The method of claim 30, wherein the adsorbent regeneration step is carried out at an absolute pressure in the range of about 0.2 to about 1 bar.

* * * * *